United States Patent [19]

Tanaka

[11] Patent Number: 4,563,588
[45] Date of Patent: Jan. 7, 1986

[54] APPARATUS FOR MEASURING THE LUMINOUS LIFETIME OF SAMPLES

[75] Inventor: Masaru Tanaka, Kyoto, Japan

[73] Assignee: Horiba, Ltd., Kyoto, Japan

[21] Appl. No.: 562,119

[22] Filed: Dec. 16, 1983

[30] Foreign Application Priority Data

Jan. 8, 1983 [JP] Japan ............................... 58-2143[U]

[51] Int. Cl.$^4$ ...................... G01T 1/10; H03K 5/159; H03K 17/00
[52] U.S. Cl. ................................ 250/458.1; 307/353; 328/151
[58] Field of Search .................. 307/247 R, 244, 352, 307/353, 600, 602; 328/129.1, 130.1, 151, 153; 250/255, 458.1, 459.1, 461.1, 461.2

[56] References Cited

U.S. PATENT DOCUMENTS

| | | | |
|---|---|---|---|
| 3,428,828 | 2/1969 | Korzekwa et al. | 307/353 |
| 4,198,567 | 4/1980 | Eneroth et al. | 250/459.1 |
| 4,464,568 | 8/1984 | Brown et al. | 250/253 |

Primary Examiner—Alfred E. Smith
Assistant Examiner—V. Lemmo
Attorney, Agent, or Firm—Wenderoth, Lind & Ponack

[57] ABSTRACT

An apparatus for measuring the luminous lifetime samples, which eliminates the deviation of the time axis of each channel of a multichannel TAC, deviations resulting from differences the wiring or the time lag of the elements of each channel of the multichannel TAC constituting a principal part of the apparatus. The apparatus operates by adding a respective variable offset voltage to the output of each channel of the TAC and by regulating the offset voltage in every channel without using any delay element so as to eliminate the time axis deviations of the channels.

3 Claims, 3 Drawing Figures

are successively reset, and the time-to-amplitude conversions are stopped one after another. Since the output voltages of the "TACs" in the respective channels are the final charging voltages of the respective capacitors, as shown in FIG. 2, they are voltages which are proportional to the time lapses from the times when the start pulses $P_A$ have been supplied until the respective stop pulses $P_{B1}$, $P_{B2}$ . . . are supplied.

APPARATUS FOR MEASURING THE LUMINOUS LIFETIME OF SAMPLES

BACKGROUND OF THE INVENTION

1. Field of the Invention

This invention relates to an apparatus for measuring the luminous lifetime of samples, and more particularly, to the improvements in a multichannel Time-to-Amplitude Converter (hereinafter referred to as a "TAC") which constitutes the principal part of the apparatus.

2. Description of the Prior Art

The measurement of the luminous lifetime of samples is usually made by detecting, with the aid of a photomultiplier tube, for example, the fluorescent pulse being emitted from a sample which is excited by a pulse of light, and by observing the time lapse from the leading edge of the pulse-excited light until the fluorescent pulse is emitted. In this case, since the mere measurement of time is unfit for the later treatment of signals, it is necessary to convert the time detected to an amplitude proportional to the above-mentioned time lapse from the leading edge of the pulse-excited light until the fluorescent pulse is emitted, wherefore the "TAC" is employed. Incidentally, the measurement of the luminous lifetime can be simplified sharply if it would be possible to measure all of the plurality of luminous pulses being emitted by a single excitation and to convert the measurements from time to amplitude. A multichannel "TAC" is capable of measuring all of a plurality of luminous pulses excited in such a way and of converting the measurements from time to amplitude. This multichannel "TAC" is provided with many channels (8 channels in the illustrated example in FIG. 1) such as "TAC" 1 consisting of a flip-flop $FF_1$, a constant-current regulated power supply $I_1$, a charging capacitor $C_1$, a switch $SW_1$ for regulating the changeover of the charging current to the capacitor $C_1$, and a sample and hold circuit $SH_1$ for sampling and holding the final charging voltage of the capacitor $C_1$. Each of the flip-flops $FF_1$, $FF_2$ . . . is set by the start pulse $P_A$ being emitted at the leading edge of the pulse-excited light. When the flip-flops $FF_1$, $FF_2$ . . . are set, the switches $SW_1$, $SW_2$ . . . are turned ON, and the capacitor $C_1$, $C_2$. . . start charging, that is, when the respective start pulse $P_A$ is supplied, all of the channels start the time-to-amplitude conversion. Next, when the luminous pulse $P_{B1}$ used as the stop pulse is supplied, the flip-flop $FF_1$ in the first channel is reset, and the switch $SW_1$ is turned OFF. The flip-flops of the remaining channels are not reset by a first single stop pulse because the gate circuits $G_1$, $G_2$ . . . are inserted in the respective reset input lines.

By the above-mentioned $SW_1$ being turned OFF, the charging of the capacitor $C_1$ is stopped, and the time-to-amplitude conversion is ended and the charging voltage is held by the sample and hold circuit $SH_1$. On the other hand, by the flip-flop $FF_1$ being reset, the gate circuit $G_1$ provided on the reset input of the second channel is enabled. According, the second stop pulse is supplied to flip-flop $FF_2$ of the second channel so as to reset it, and the switch $SW_2$ is turned OFF; at the same time, the gate circuit $G_2$ on the reset input of the third channel is also enabled. By the switch $SW_2$ being turned OFF, the charging of the capacitor $C_2$ is ended and the charging voltage is held by the sample and hold circuit $SH_2$.

Hereinafter, every time, whenever the third and fourth, etc., stop pulses are supplied, the flip-flops $FF_3$, $FF_4$ . . . are successively reset, and the time-to-amplitude conversions are stopped one after another.

Hereupon, in the above-mentioned multichannel "TAC", although it is not possible for any "TAC" to start the conversion instantaneously when the start pulse $P_A$ is inputted thereto, and to stop the conversion instantaneously when its corresponding stop pulse is inputted, yet in practice there are some differences in length among the wires to each of the flip-flops $FF_1$, $FF_2$ . . . , and in the lag time of each of the gate circuits. Since the time intervals from the start pulses to the stop pulses are on the order of nanoseconds, there arises a problem that in each of the channels, the time interval after the conversion starts until it comes to an end does not exactly correspond to the time interval from the start pulse to the stop pulse, the interval being accompanied by an error which varies from channel to channel. This problem may be grasped, in other words, as a problem in that the time axis of each channel gets out of position due to the time delays of the wiring or of the elements. The time axis error of this type can be eliminated by inserting the delay elements $\tau_1, \tau_2, \tau_3$ . . . on the input side of the "TAC" in every channel, as shown in FIG. 1 and by thereby individually regulating the delay time in every element. However, even with such means, the following defects remain:

1—Each delay element must continuously vary the delay time; however, such a delay element is very expensive, particularly for use with high speed pulses.

2—Although it is preferable to bring the setting knob of the delay element to the front panel of the system, because there is a necessity of properly regulating the delay time, it is impossible to electrically extend the delay element as far as the front panel and away from the circuitboard since high-speed pulses are passed through the delay element. For this reason, there is no choice but to use a cumbersome unreliable method as to mechanically extend the shaft of the delay element control knob, leaving the delay element mounted on the circuitboard.

SUMMARY OF THE INVENTION

In the light of the above-mentioned problems, this invention has for its object to simplify the alignment of the time axis of every channel after the time-to-amplitude conversion, or more precisely, to simplify the alignment of the time axis by adding a variable offset voltage to the voltage being outputted from the "TAC" of each channel, and by regulating this offset voltage, thereby eliminating each of the above-mentioned defects of the prior art.

DESCRIPTION OF THE PREFERRED EMBODIMENT

Description will be now directed to an example of the present invention with reference to the drawings.

Figure 1:
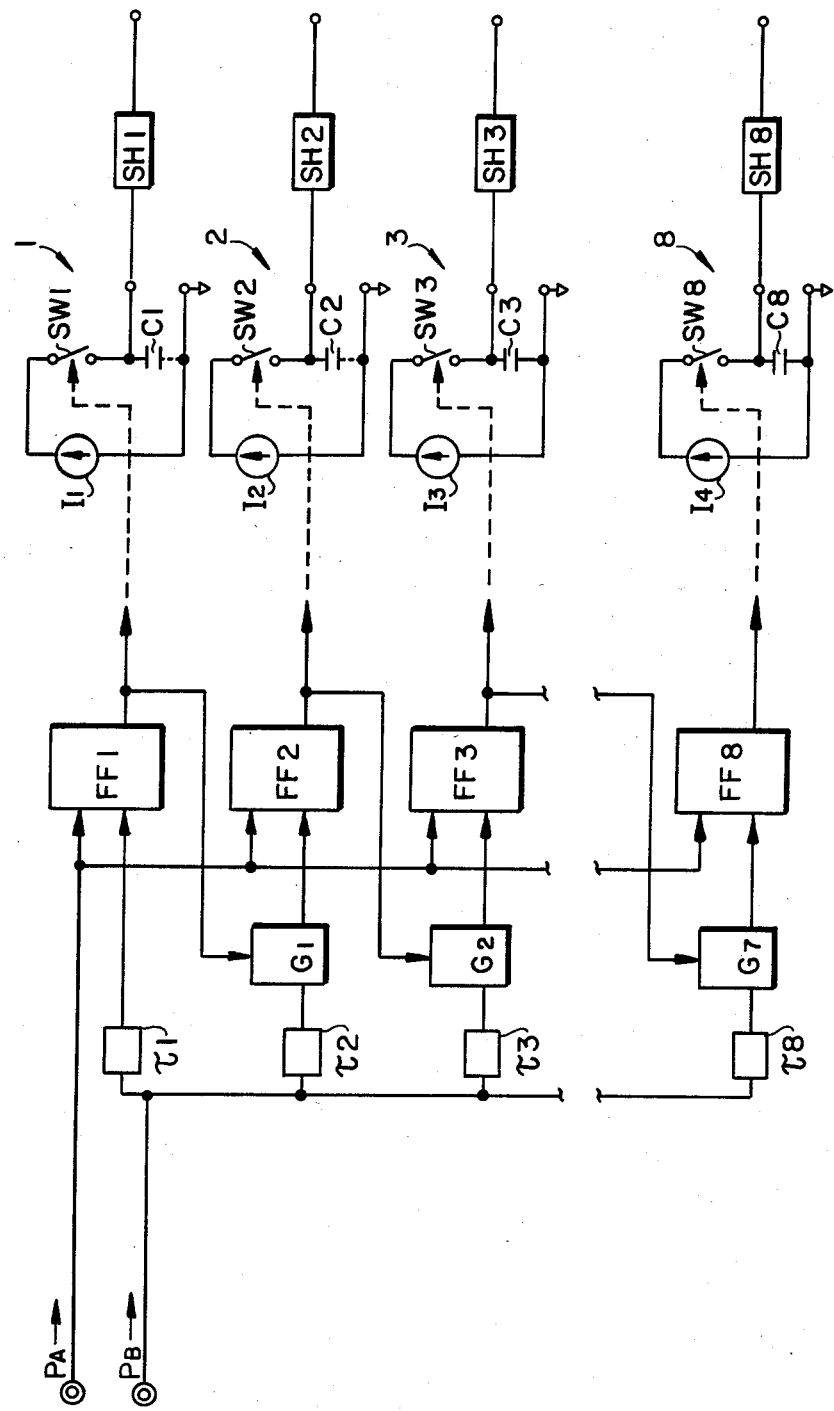
FIG. 1 is a circuit diagram showing a multichannel "TAC" according to conventional art which is provided with delay elements.
Figure 3:
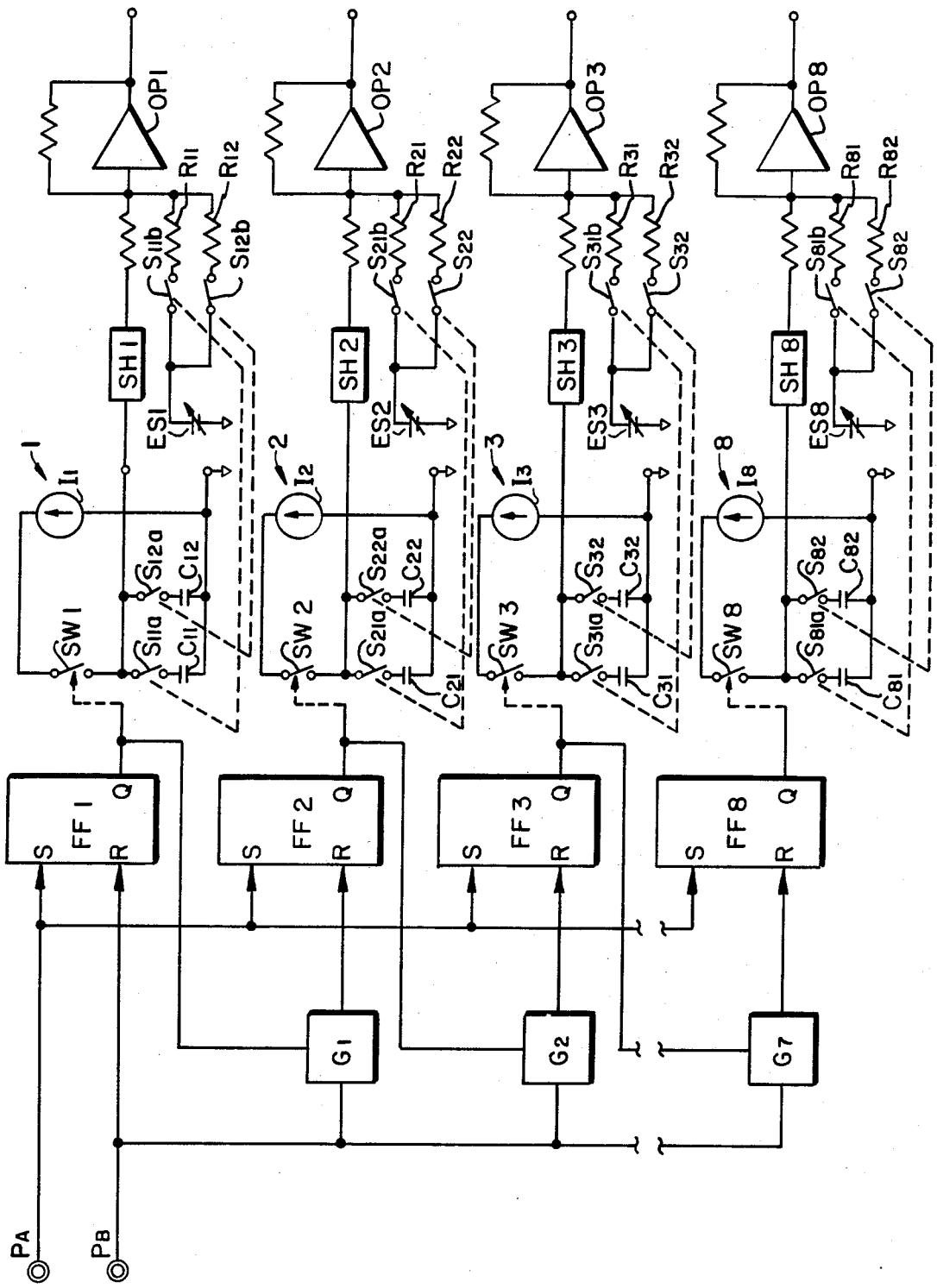
FIG. 3 is a circuit diagram showing an embodiment of a multichannel "TAC" in accordance with the present invention.

FIG. 3 shows an example of the present invention. In the figure, the elements equal to those of the multichannel "TAC" of FIG. 1 are given the same numerals. Voltages $ES_1$, $ES_2$, $ES_3$ ... are variable offset voltages, which are added to the output voltages of the respective $TAC_{1, 2, 3}$ ... of the respective channels, namely, to the respective output voltages of the sample and hold circuits $SH_{1, 2, 3}$ .... Elements $OP_1$, $OP_2$ ... are adders which add the respective offset voltages $ES_1$, $ES_2$ ... to the output voltages of $TAC_{1, 2}$ ... so as to produce respective outputs. EAch of the elements $TAC_{1, 2}$ ... is provided with a plurality (2 in the illustrated example) of capacitors $C_{11}$, $C_{12}$ of different capacities used as the charging capacitors and is so arranged that the range selection can be done by changing-over each of the capacitors $C_{11}$, $C_{12}$ ... by the switches $S_{11}a$, $S_{12}a$. In this case, supposing that the offset voltages $ES_1$, $ES_2$ ... are fixed and unchangeable throughout before and after the range selection, even though those offset voltages have been regulated, and their time axes have been aligned before the range selection, yet the time axes come to be out of alignment. For this reason, in the example, by inserting the switches $S_{11}b$, $S_{12}b$ which are interlocked with the range-selecting switches $S_{11}a$, $S_{12}a$, on the one side, and the range resistances $R_{11}$, $R_{12}$ for use in adding the offset voltages correspondent to the range ratios, on the other side, in series with the offset voltages $ES_1$, $ES_2$ ..., it is so arranged that the offset voltages being added to the output voltages of the sample and hold circuits $SH_1$, $SH_2$ ... vary corresponding to the range ratios before and after the range selection, whereby the time axes should not be out of alignment before and after the range selection.

Figure 2:
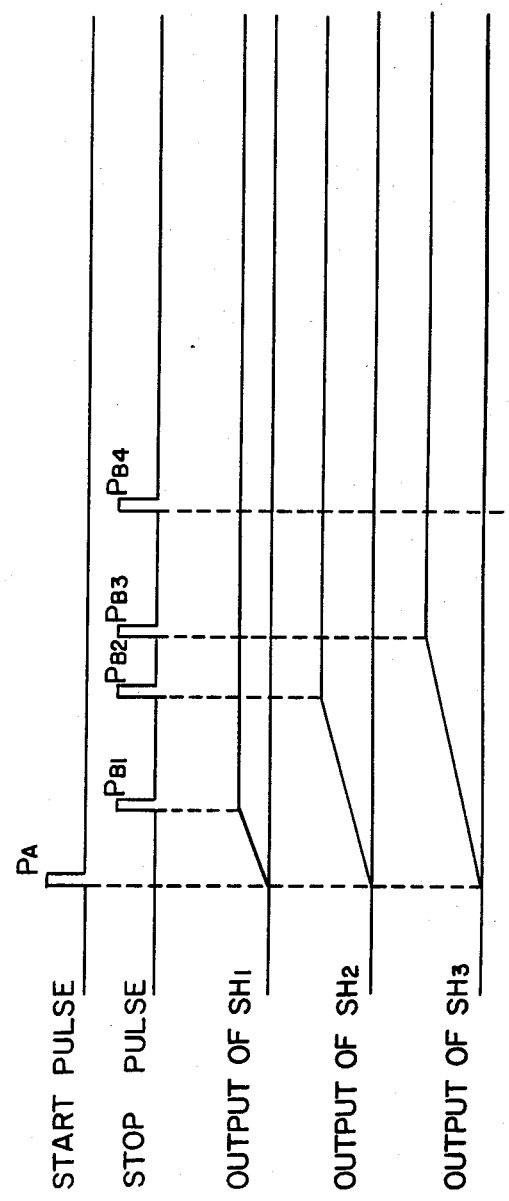
FIG. 2 is a diagram explaining the operation of FIG. 1.

The reason why the alignment of the time axes is practicable by making the offset voltages variable, as in this example, can be interpreted on the basis of the output voltages of the sample holds shown in FIG. 2 as follows:

If the offset voltages are added, the output voltages of the sample holds $SH_1$, $SH_2$ ... are heightened or lowered as much as the portions of the offset voltages. The rise of the output voltage of the sample hold means the substantial prolongation of the time interval between the starting of the conversion of the "TAC" and the stopping of it, and conversely the fall of the output voltage signifies the curtailment of the time interval. In this way, the substantial occurrence of such a variation of the time interval, now longer and now shorter, is equal to the delay function of the delay element, and consequently it implies that it is possible to make the alignment of the time axis on the basis of the offset voltage.

As described in the above, this invention is provided with the time-to-amplitude converter in the form of a multichannel converter. The individual time-to-amplitude converter in each channel starts the conversion when the start pulse is fed thereto. The time-to-amplitude converter in the first channel stops the conversion when the first stop pulse is fed thereto, and the time-to-amplitude onverter in the second channel stops the conversion when the second stop pulse is fed thereto. It is arranged so that hereinafter the other time-to-amplitude converters in the succeeding channels likewise stop their own conversions in order each time that the stop pulse in fed thereto. With such an arrangement, the apparatus for measuring the luminous lifetime of samples according to the present invention is so devised that the luminous lifetime of the sample will be measured on the basis of the voltage output of the converter in each channel which has stopped its conversion, wherein the variable offset voltage is added to the output of the time-to-amplitude converter in each channel, and that the offset voltage is regulated in every channel, and the alignment of the time axis in every channel can thereby be effected, so that this apparatus has the following advantages:

1—There is no necessity for inserting a delay element in the circuit through which the high-speed pulse is to pass, so that a degeneration of the pulse risetime or falltime does not occur.

2—Because a DC voltage called the offset voltage performs the alignment of the time axis, it is not affected electrically even if transmitted over relatively long lines. Therefore, it becomes easier to design the apparatus. That is, remote control of the offset voltages by front panel controls are easily constructed.

3—The use of a DC voltage as the offset voltage, allows the fabrication of the apparatus at a very low cost, and the variable time delay width can be wide as compared with that of the prior art delay element. In particular, if the voltage range is widened so as to vary up to the range of negative voltages, the regulation can reach even as far as a range which is unfeasible at all with the prior art delay element.

4—Further, there is a limitation for the delay element that the high-speed pulse must have more than a fixed pulse width in order to carry out the delaying motion, in contrast with the present invention which is not subject to such a limitation in the least.

I claim:

1. In an apparatus for measuring the luminous lifetime of samples comprising a multichannel time-to-amplitude converter having N channels numbered 1 through N wherein N is a positive integer, said converter comprising a start pulse input means for receiving a start pulse and a stop pulse input means for receiving a plurality of stop pulses, wherein each of said channels includes a flip-flop having its set input connected to said start pulse input means and having an output connected to a time-to-amplitude converter connected to a sample and hold means; and wherein said flip-flop of channel 1 has a reset input connected to said stop pulse input means and said channels 2 through N are arranged such that reset inputs of their respective flip-flops are connected to said stop pulse input means through corresponding gate means, each corresponding gate means of channel N having an enabling input connected to and controlled by a corresponding flip-flop of said channel $N-1$ such that said start pulse sets all of said flip-flops and a first stop pulse resets said first flip-flop and a second stop pulse resets said second flip-flop ... and N stop pulse resets said N flip-flop, the improvement comprising:
 a plurality of voltage adders each connected to a corresponding sample and hold means;
 a plurality of variable offset voltage means each connected to a corresponding one of said plurality of adder means wherein each offset voltage may be manually adjusted so as to compensate for errors in a time axis of its corresponding channel.

2. An apparatus as in claim 1, wherein said time-to-amplitude converter channels are arranged to have at least two ranges and wherein each of said offset voltages is arranged to have a different value for each of said ranges.

3. An apparatus as in claim 1, wherein each of said time-to-amplitude converter means comprises a current source controlled by a switching means which charges a capacitor, a voltage across said capacitor feeding said sample and hold circuit.

* * * * *